United States Patent
Fleming, III et al.

(10) Patent No.: US 7,655,037 B2
(45) Date of Patent: Feb. 2, 2010

(54) COMBINATION BARB RESTRAINT AND STENT ATTACHMENT DEPLOYMENT MECHANISM

(75) Inventors: James A. Fleming, III, Bethlehem, PA (US); David C. Majercak, Stewartsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 124 days.

(21) Appl. No.: 12/104,727

(22) Filed: Apr. 17, 2008

(65) Prior Publication Data
US 2009/0264992 A1    Oct. 22, 2009

(51) Int. Cl.
*A61F 2/06* (2006.01)
(52) U.S. Cl. ................ 623/1.36; 623/1.35
(58) Field of Classification Search ........... 623/1.12, 623/1.35, 1.36; 606/151, 153, 191, 192, 606/194, 198
See application file for complete search history.

(56) References Cited

U.S. PATENT DOCUMENTS

| | | | | |
|---|---|---|---|---|
| 5,387,235 A | * | 2/1995 | Chuter | 623/1.11 |
| 5,562,726 A | * | 10/1996 | Chuter | 623/1.35 |
| 5,851,228 A | * | 12/1998 | Pinheiro | 623/1.13 |
| 6,451,051 B2 | * | 9/2002 | Drasler et al. | 623/1.15 |
| 6,517,573 B1 | * | 2/2003 | Pollock et al. | 623/1.15 |
| 6,814,748 B1 | * | 11/2004 | Baker et al. | 623/1.14 |
| 2002/0022853 A1 | * | 2/2002 | Swanson et al. | 606/155 |
| 2002/0091439 A1 | * | 7/2002 | Baker et al. | 623/1.36 |
| 2003/0220683 A1 | | 11/2003 | Minasian et al. | |
| 2005/0010277 A1 | * | 1/2005 | Chuter | 623/1.13 |
| 2005/0137687 A1 | * | 6/2005 | Salahieh et al. | 623/2.11 |
| 2005/0159803 A1 | * | 7/2005 | Lad et al. | 623/1.13 |
| 2006/0025850 A1 | * | 2/2006 | Feller et al. | 623/1.16 |
| 2006/0095116 A1 | * | 5/2006 | Bolduc et al. | 623/1.16 |
| 2007/0173929 A1 | * | 7/2007 | Boucher et al. | 623/1.35 |
| 2008/0021544 A1 | * | 1/2008 | Majercak et al. | 623/1.36 |
| 2009/0204202 A1 | * | 8/2009 | Dierking et al. | 623/1.16 |
| 2009/0234429 A1 | * | 9/2009 | Lau | 623/1.12 |
| 2009/0234430 A1 | * | 9/2009 | Fleming et al. | 623/1.13 |

FOREIGN PATENT DOCUMENTS

| | | |
|---|---|---|
| EP | 0747020 B1 | 12/1996 |
| EP | 1621159 A1 | 2/2006 |
| EP | 1810642 B1 | 7/2007 |

OTHER PUBLICATIONS

European Search report dated Jul. 22, 2009 for corresponding Application No. EP09251101.

* cited by examiner

*Primary Examiner*—Corrine M McDermott
*Assistant Examiner*—Tiffany Shipmon
(74) *Attorney, Agent, or Firm*—Carl J. Evens

(57) ABSTRACT

An aneurysmal repair system that utilizes a modified apex and delivery device is designed for accurate endoprosthesis delivery and deployment. The modified apex utilizes segments that overlap and hold one another down as well as the fixation barbs attached thereto. The delivery device holds or secures at least one section of the apex and may be easily released by retraction of a hold down member.

9 Claims, 15 Drawing Sheets

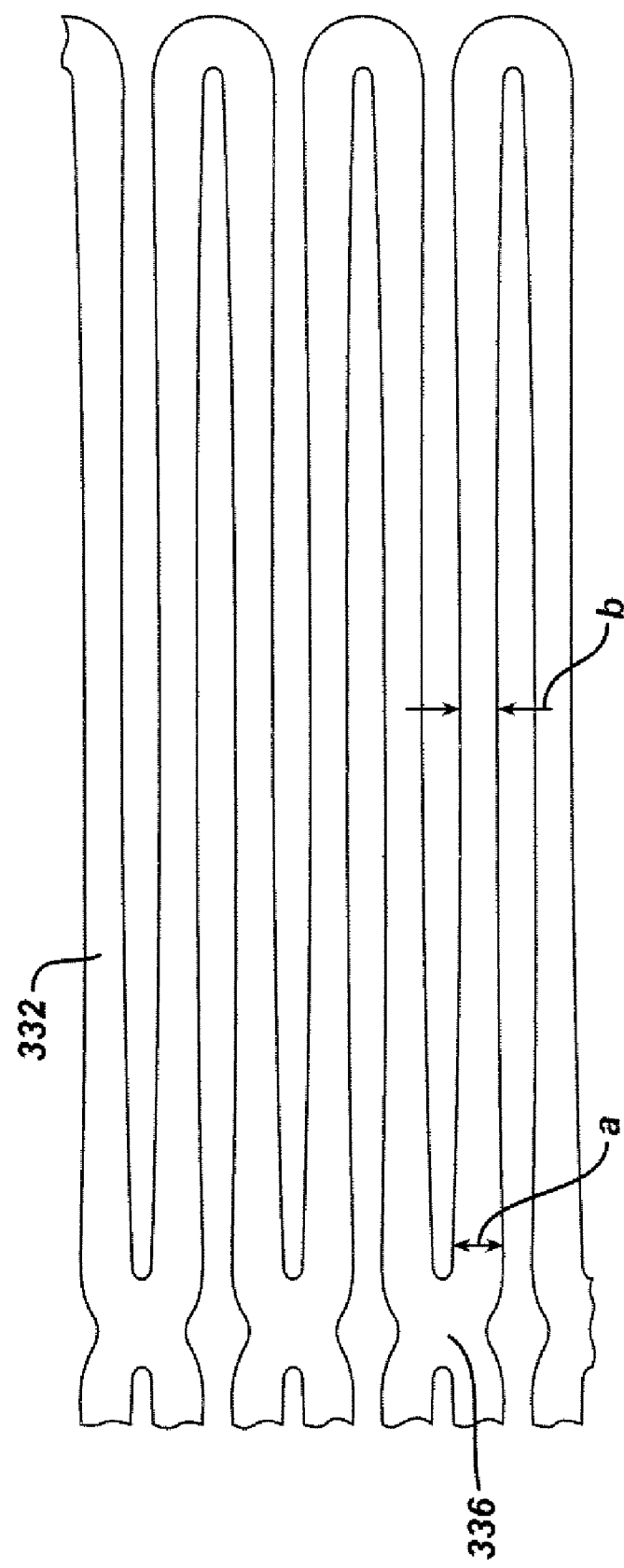

COMBINATION BARB RESTRAINT AND STENT ATTACHMENT DEPLOYMENT MECHANISM

BACKGROUND OF THE INVENTION

1. Field of the Invention

The present invention relates to aneurismal repair devices, and more particularly, to devices that facilitate the restraint and selective deployment of the cranial end of an aneurismal repair device during delivery.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via a transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3 F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be highly durable, extendable and re-configurable while maintaining acute and long-term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta. In addition, the endoprostheses should preferably be percutaneously delivered and deployed such that surgical cut down is unnecessary.

Many aneurismal repair devices currently in the market utilize a woven Dacron® graft material and a metallic stent or scaffold. Typically, the stents are attached to the graft material by sutures. Even though the stents are sutured in place, this does not completely eliminate relative movement between the stent and the graft material caused by the pulsatile movement of the blood in the particular artery and the movement of the artery itself. This relative motion between the stent and the graft causes wear and potentially a separation or opening between the graft and the stent. This potential separation or opening may in turn lead to endo leaks. Accordingly, it would be highly advantageous to develop a system for preventing this or substantially eliminating relative movement between the stent and the graft.

Many aneurismal repair devices have deployment systems that address two significant concerns individually or not at all. The two significant concerns are accurate stent deployment and fixation barb restraint. Accordingly, a design is needed to allow for the restraint and selective deployment of the cranial end of an endoprosthesis during delivery while also restraining the fixation barbs from deploying before the prosthesis has centered itself in the target vessel during deployment.

SUMMARY OF THE INVENTION

The present invention overcomes the disadvantages associated with currently utilized aneurismal repair devices.

In accordance with one aspect, the present invention is directed to an aneurysm repair system. The repair system comprises at least one substantially cylindrical stent segment, the at least one substantially cylindrical stent segment having modified apexes, the modified apexes including first sections, second sections and fixation barbs, the second sections being configured to overlap and restrain the fixation barb on an adjacent apex, and graft material affixed, via attachment elements, to at least a portion of the at least one substantially cylindrical stent segment.

In accordance with another aspect, the present invention is directed to a stent. The stent comprising at least one substantially cylindrical stent segment having modified apexes, the modified apexes including first sections, second sections and fixation barbs, the second sections being configured to overlap and restrain the fixation barb on an adjacent apex.

In accordance with yet another aspect, the present invention is directed to a stent system. The stent system comprising at least one substantially cylindrical stent segment having modified apexes, the modified apexes including first sections, second sections and fixation barbs, the second sections being configured to overlap and restrain the fixation barb on an adjacent apex, and a securing mechanism having at least one protruding member configured for placement in at least one of the second sections and a hold down member connected on one end to the at least one protruding member and on the other end to a pull back mechanism.

The present invention is directed to a combination barb restraint and stent deployment mechanism. The exemplary stents of the present invention include modified apexes wherein one section of the modified apex holds down the fixation barbs on an adjacent apex. With this design, the proximal end of an endoluminal prosthesis may be restrained with one or more fingers attached to a member that is pulled free from the assembly when the device is deployed.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 4C is an enlarged plan view of a section of the stent segment of FIG. 4.

DETAILED DESCRIPTION OF THE PREFERRED EMBODIMENTS

Figure 1:
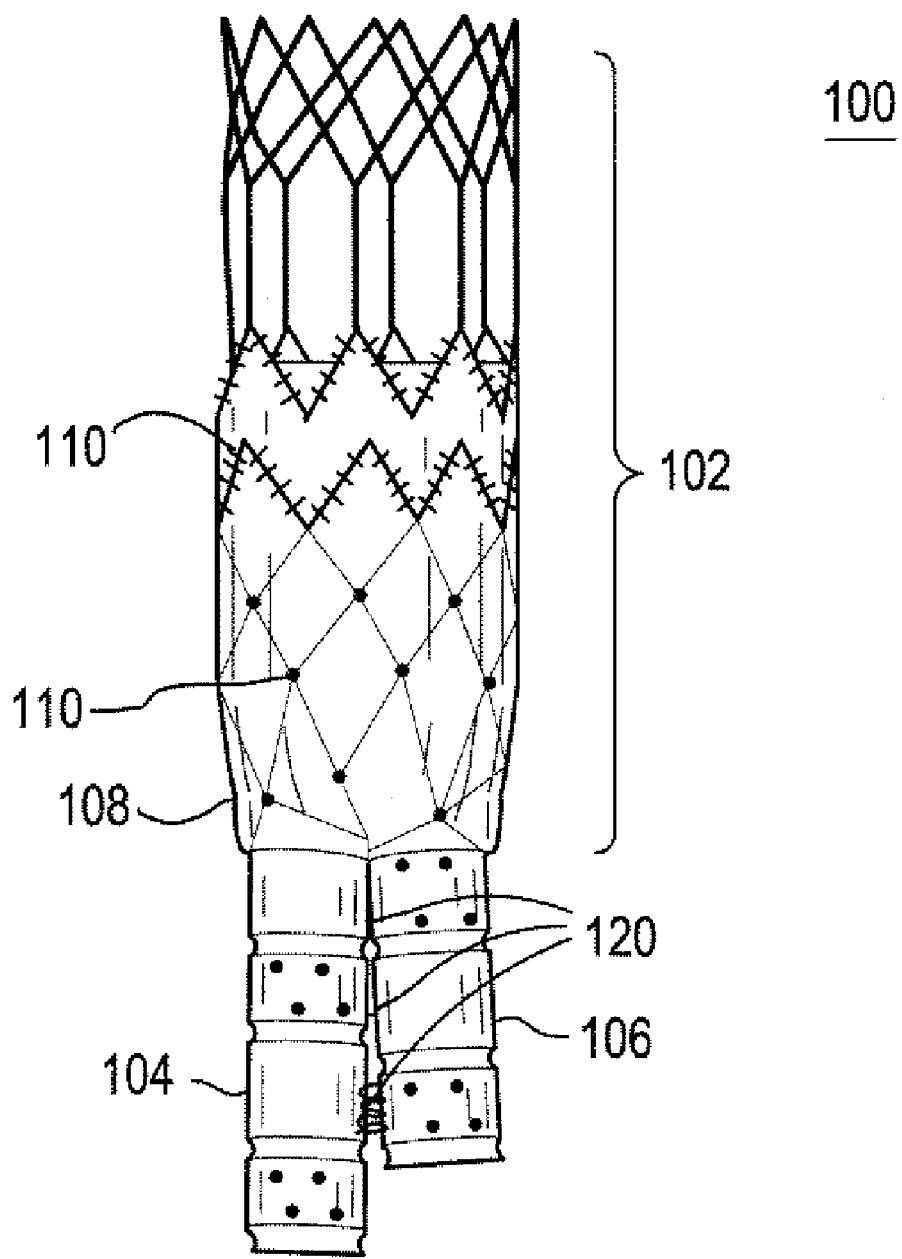
FIG. 1 is a diagrammatic representation of the exemplary anchoring and sealing prosthesis in accordance with the present invention.

Referring to FIG. 1, there is illustrated an exemplary embodiment of an anchoring and sealing component 100 of an aneurysm repair system. The anchoring and sealing component 100 comprises a trunk section 102 and a bifurcated section, including two legs 104, 106. Graft material 108, described in detail below, is affixed to at least a portion of the trunk section 102 and to all of the legs 104, 106. The graft material may be attached via any number of means. In the exemplary embodiment, the graft material 108 is attached to various portions of the underlying structure by sutures 110. As illustrated, the graft material 108 is affixed with a continuous stitch pattern on the end of the trunk section 102 and by single stitches elsewhere. It is important to note that any stitch pattern may be utilized, and other devices, such as staples, may be utilized to connect the graft material 108 to the underlying structure. The sutures 110 may comprise any suitable biocompatible material that is preferably highly durable and wear resistant.

Figure 2:
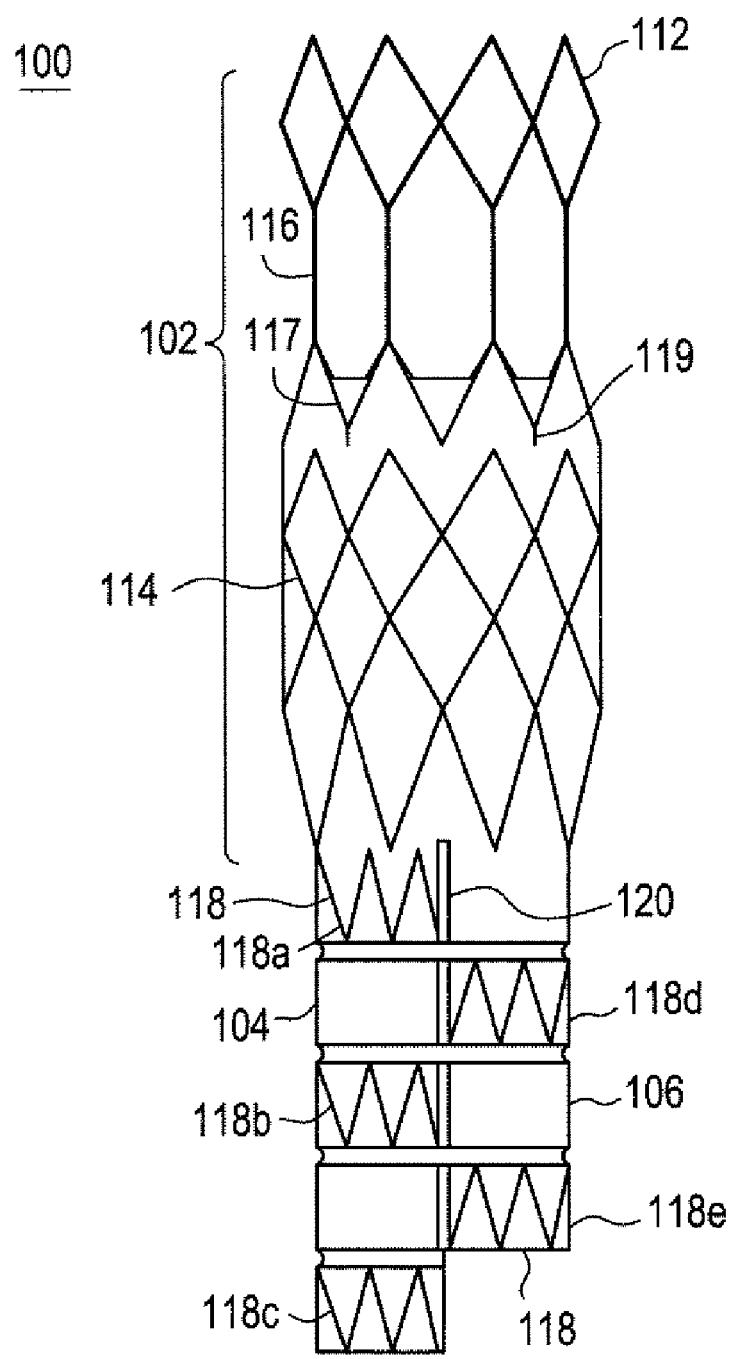
FIG. 2 is a diagrammatic representation of an exemplary anchoring and sealing prosthesis with no graft material and/or stitching in certain locations in accordance with the present invention.

The underlying structure of the trunk section 102, as illustrated in FIG. 2, comprises a substantially tubular stent structure or lattice comprising multiple stent sections. The stent or lattice structure comprises a single row of substantially diamond shaped elements 112 on one end, multiple rows of substantially diamond shaped elements 114 on the other end, a plurality of longitudinal struts 116 and a single, substantially zigzag shaped stent element 117. The plurality of longitudinal struts 116 are connected to the apexes of the substantially diamond shaped elements 114. The single, substantially zigzag shaped stent element 117 comprises a number of barbs 119 protruding therefrom for anchoring the device in the vessel to be repaired. This exemplary embodiment may be utilized for anchoring and sealing in positions wherein there are branches off the main artery. For example, this exemplary embodiment may be utilized for supra-renal anchoring. Accordingly, the graft material 108 is only attached below the longitudinal struts 116 so that blood may flow into the renal arteries from the aorta. Infra-renal designs are also possible.

The underlying structure of the bifurcated section, as illustrated in FIG. 2, comprises a plurality of individual, substantially tubular stent elements 118. Each stent element 118 comprises a substantially zigzag pattern. As illustrated, leg 104 comprises three stent elements 118a, 118b, 118c and leg 106 comprises two stent elements 118d, 118e. As illustrated, in this exemplary embodiment, the stent elements do not line up and the legs are of two different lengths. This exemplary design allows for nesting of the legs 104, 106 such that the profile of the device is reduced.

In order to compensate for the missing stent elements, the legs are connected at the bifurcation as illustrated in FIG. 1. The legs 104, 106 may be connected in any suitable manner. In the exemplary embodiment, the two legs 104, 106 are connected by suturing them together. The sutures 120 connect the graft material 108 on each leg 104, 106 together. The sutures may be non-biodegradable or biodegradable. Biodegradable sutures would dissolve over time thereby allowing the two legs to move independently.

Figure 3:
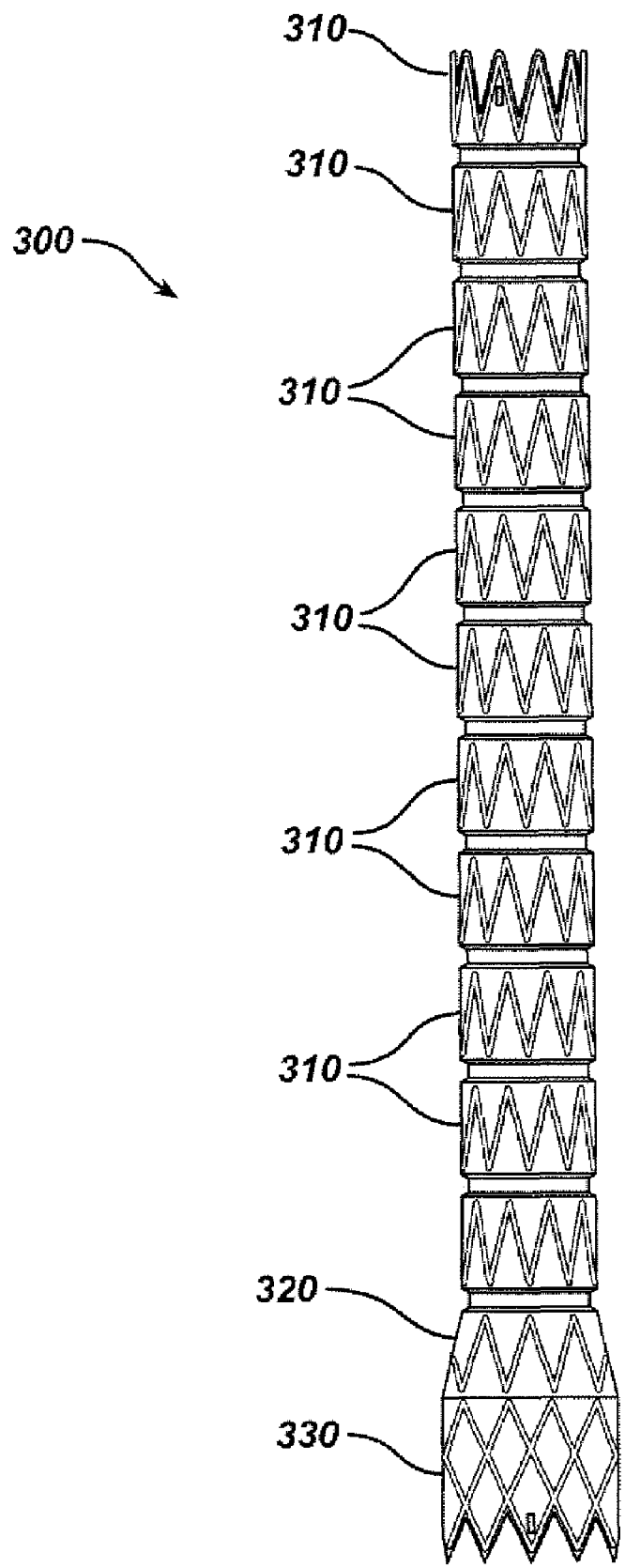
FIG. 3 is an elevational view of an endovascular graft in accordance with the present invention.

Referring now to FIG. 3, there is illustrated an exemplary embodiment of an endovascular graft 300 of an aneurysm repair system. The exemplary endovascular graft 300 comprises one or more first stent segments 310, one second stent segment 320 and a third stent segment 330. In a typical use scenario, the third stent segment 330 would be anchored in healthy tissue below the aneurysm and the uppermost first stent segment 310 would be in fluid communication with the anchoring and sealing component 100. The second stent segment 320 comprises a tapered profile, having a diameter at one end equal to that of the first stent segment 310 and a diameter at the other end equal to that of the third stent segment 330. The length of the endovascular graft 300 may be adjusted by varying the number of first stent segments 310 utilized.

Figure 4:
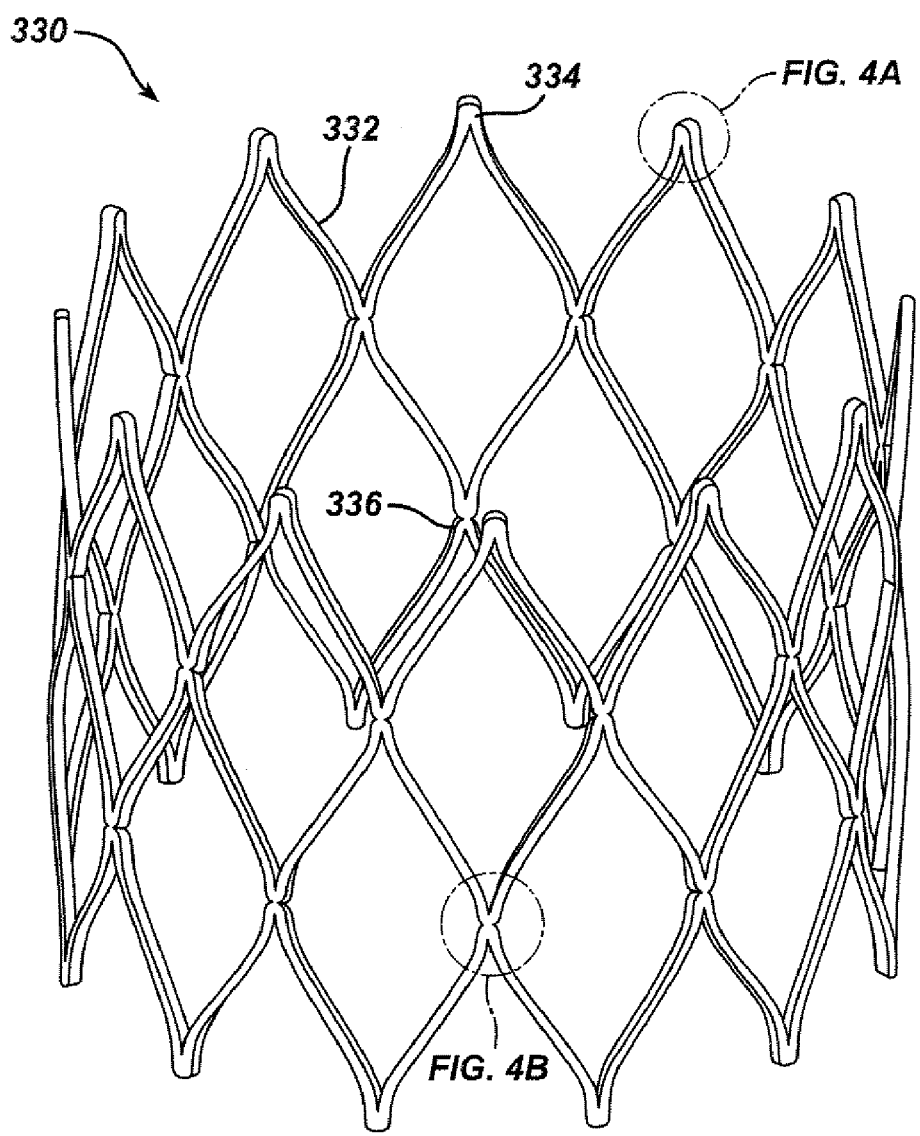
FIG. 4 is a perspective view of an expanded stent segment of the endovascular graft in accordance with the present invention.
Figure 4A:
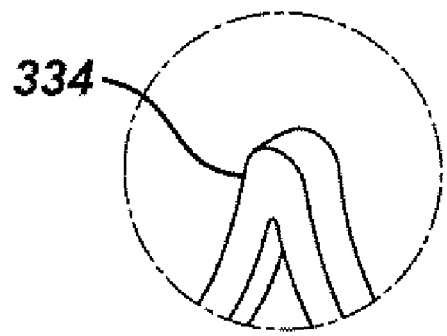
FIG. 4A is a fragmentary perspective view of a portion of the stent segment of FIG. 4.
Figure 4B:
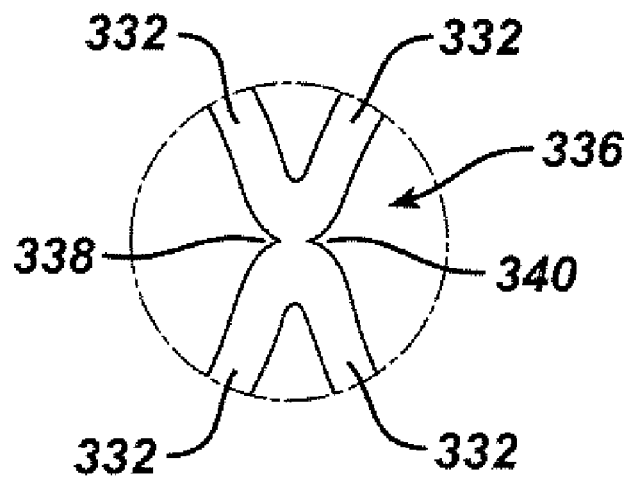
FIG. 4B is a fragmentary perspective view of a portion of the stent segment of FIG. 4.

FIG. 4 is a detailed perspective view of an exemplary embodiment of the third stent segment 330. The third stent segment 330 comprises a plurality of struts 332 connected in a substantially zigzag pattern. As illustrated, the exemplary third stent segment 330 comprises three sets of zigzag-connected struts 332, thereby forming substantially diamond-shaped cells. The non-connected apex 334 of each diamond shaped cell, illustrated in greater detail in FIG. 4A, comprises a smooth, uniform width curved region formed at the intersection of two struts 332 of each diamond-shaped cell. This shape is cut directly into the stent segment 330 during the initial machining steps, typically laser cutting, and is maintained during all subsequent finishing processing. The junctions 336 between the zigzag-connected struts 332, illustrated in greater detail in FIG. 4B occurs at the intersection of four struts 332. Preferably, each junction 336 of four struts 332 comprises two indentations 338 and 340 as illustrated in FIG. 4B.

The regions proximate the non-connected apexes 334 and the junctions 336 are generally the highest stress regions in the third stent segment 330. To minimize the stresses in these regions, these regions are designed to maintain uniform beam widths proximate where the struts 332 interconnect. Beam width refers to the width of a strut junction 336. Indentations 338 and 340 are cut or machined into the junctions 336 to maintain a uniform beam width in this area, which is generally subject to the highest stress. Essentially, by designing the junctions 336 to maintain uniform beam widths, the stress and strain that would normally build up in a concentrated area, proximate the junction 336, is allowed to spread out into the connecting regions, thereby lowering the peak values of the stress and strain in the stent structure.

To further minimize the maximum stresses in the struts 332 of the third stent segment 330, the struts 332 may have a tapering width. For example, in one exemplary embodiment, the struts 332 may be designed to become wider as it approaches a junction 336. FIG. 4C is an enlarged partial view of the third sent segment 330 in its expanded conditions which illustrates the tapering width of the struts 332. In this exemplary embodiment, the strut 332 proximate the junction 336 (width a) is about 0.025 cm and gradually tapers to a dimension of about 0.0178 cm in the mid-region of the strut 332 (width b). By tapering the struts' widths, the stresses in the struts 332 adjacent the junction 336 is spread out away from the junction 336. The tapering of the struts 332 is accomplished during the machining of the tube of material from which the stent 330 is cut. However, by tapering the struts 332 in this manner, there is a tradeoff. The stent segment 330 becomes somewhat less resistant to localized deformations, caused for example, by a protrusion within the vessel lumen. This localized deformation may lead to a local torsional loading on some of the struts 332, and, therefore, since the struts 332 in this exemplary embodiment have a relatively significant portion of their length with a reduced width, their torsional rigidity is reduced.

Figure 4D:
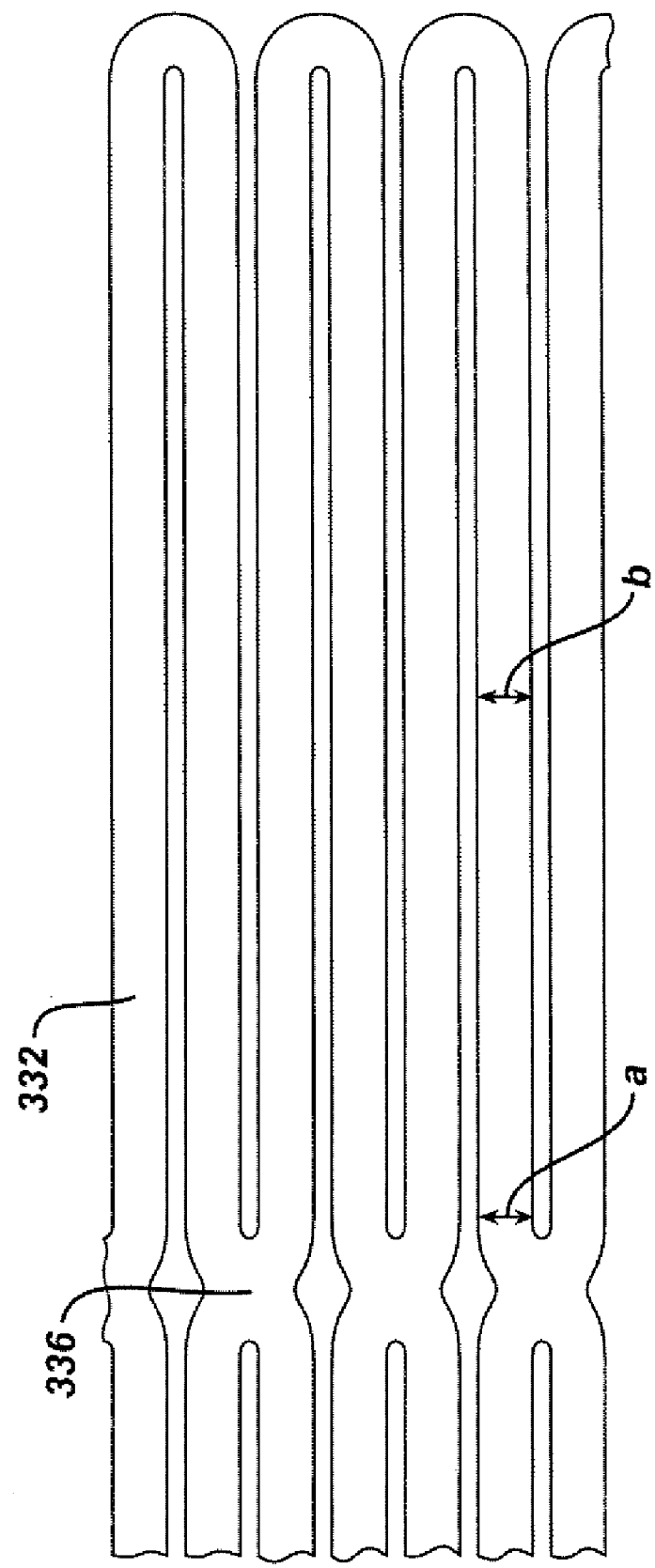
FIG. 4D is an enlarged plan view of a section of the stent segment of FIG. 4.

If maximizing the resistance to localized deformation is preferred, the struts 332 may be maintained at a uniform width, or more preferably have a reverse taper, as illustrated in FIG. 4D, wherein the width at point a is less than the width at point b. In this exemplary embodiment, the reverse taper struts 332 are about 0.025 cm proximate the junction 336 and about 0.028 cm in the central region of the struts. While this reverse taper tends to increase the stresses somewhat proximate the junctions 336, this increase is very small relative to the decrease in stresses gained by having the side indentations 338, 340 illustrated in FIG. 4B, as well as the uniform width connections illustrated in FIG. 4A. In addition, since the reverse taper serves to increase the torsional rigidity of the strut 332, the stent structure resists local deformation and tends to maintain a substantially circular cross-sectional geometry, even if the lumen into which the stent is positioned in non-circular in cross-section.

In a preferred exemplary embodiment, the third stent segment 330 is fabricated from a laser cut tube, of initial dimensions 0.229 cm inside diameter by 0.318 cm outside diameter. The struts 332 are preferably 0.0229 cm wide adjacent the four strut junctions 336 and six mm long, with a reverse taper strut width. Also, to minimize the number of different diameter combination of grafts systems, it is preferred that the third stent segment 330 have an expanded diameter of sixteen mm. Similarly, the proximal portion of the graft material forming the legs is flared, having a diameter of sixteen mm. This single diameter for the third stent segment of the graft system would enable its use in arteries having a non-aneurysmal region of a diameter from between eight and fourteen mm in diameter. It is also contemplated that multiple diameter combinations of third stent segment 330 and graft flare would be desirable.

Figure 5:
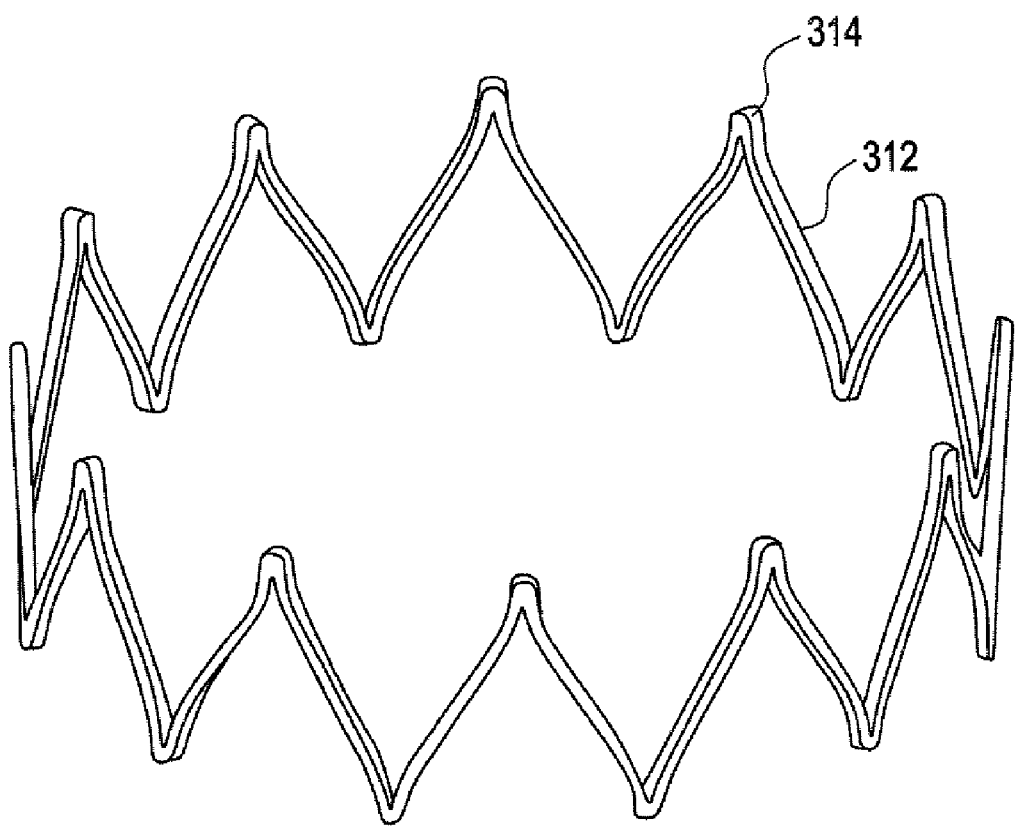
FIG. 5 is a perspective view of another expanded stent segment of the endovascular graft in accordance with the present invention.

Referring back to FIG. 3, the one or more first stent segments 310 are also formed from a shape set laser cut tube, similar to the third stent segment 330 described above. The one or more first stent segments 310 comprise a single circumferential row of zigzag or sinusoidally arranged elements. In the exemplary embodiment illustrated in FIG. 3, and in greater detail in FIG. 5, the first stent segment 310 comprises ten zigzag or sinusoidal undulations. The one or more first stent segments 310 are formed with uniform width connections at the intersections 314 of the struts 312 forming the zigzag or sinusoidal pattern. The one or more first stent segments 310 are preferably cut from tubing having an inside diameter of 0.251 cm and an outside diameter of 0.317 cm. The strut widths are preferably about 0.33 cm wide adjacent strut intersections 314 and the struts 312 are preferably seven mm long and the one or more first stent segments 310 are preferably eleven mm in diameter when expanded.

The second stent segment 320 comprises a tapered profile, having a diameter at one end which is the same as the one or more first stent segments 310, and a diameter at the other end matching the diameter of the third stent segment 330. The second stent segment 320 is identical to the one or more first stent segments 310 except for the taper.

As is explained in detail subsequently, the stent segments 310, 320 and 330 are secured in position by the graft material.

Nitinol is utilized in a wide variety of applications, including medical device applications as described herein. Nitinol or Ni—Ti alloys are widely utilized in the fabrication or construction of medical devices for a number of reasons, including its biomechanical compatibility, its biocompatibility, its fatigue resistance, its kink resistance, its uniform plastic deformation, its magnetic resonance imaging compatibility, its constant and gentle outward pressure, its dynamic interference, its thermal deployment capability, its elastic deployment capability, its hysteresis characteristics and because it is modestly radiopaque.

Nitinol, as described above, exhibits shape memory and/or superelastic characteristics. Shape memory characteristics may be simplistically described as follows. A metallic structure, for example a Nitinol tube that is in an Austenite phase may be cooled to a temperature such that it is in the Martensite phase. Once in the Martensite, the Nitinol tube may be deformed into a particular configuration or shape by the application of stress. As long as the Nitinol tube is maintained in the Martensite phase, the Nitinol tube will remain in its deformed shape. If the Nitinol tube is heated to a temperature sufficient to cause the Nitinol tube to reach the Austenite phase, the Nitinol tube will return to its original or programmed shape. The original shape is programmed to be a particular shape by well known techniques. Superelastic characteristics may be simplistically described as follows. A metallic structure, for example, a Nitinol tube that is in an Austenite phase may be deformed to a particular shape or configuration by the application of mechanical energy. The application of mechanical energy causes a stress induced Martensite phase transformation. In other words, the mechanical energy causes the Nitinol tube to transform from the Austenite phase to the Martensite phase. By utilizing the appropriate measuring instruments, one can determine that the stress from the mechanical energy causes a temperature drop in the Nitinol tube. Once the mechanical energy or stress is released, the Nitinol tube undergoes another mechanical phase transformation back to the Austenite phase and thus its original or programmed shape. As described above, the original shape is programmed by well known techniques. The Martensite and Austenite phases are common phases in many metals.

Medical devices constructed from Nitinol are typically utilized in both the Martensite phase and/or the Austenite phase. The Martensite phase is the low temperature phase. A material in the Martensite phase is typically very soft and malleable. These properties make it easier to shape or configure the Nitinol into complicated or complex structures. The Austenite phase is the high temperature phase. A material in the Austenite phase is generally much stronger than the material in the Martensite phase. Typically, many medical devices are cooled to the Martensite phase for manipulation and loading into delivery systems, as described above with respect to stents and then when the device is deployed at body temperature, they return to the Austenite phase.

The first, second and third stent segments 310, 320, 330 are preferably self-expandable and formed from a shape memory alloy. Such an alloy may be deformed from an original, heat-stable configuration to a second, heat-unstable configuration. The application of a desired temperature causes the alloy to revert to an original heat-stable configuration. A particularly preferred shape memory alloy for this application is binary nickel titanium alloy comprising about 55.8 percent Ni by weight, commercially available under the trade designation NITINOL. This NiTi alloy undergoes a phase transformation at physiological temperatures. A stent made of this material is deformable when chilled. Thus, at low temperatures, for example, below twenty degrees centigrade, the stent is compressed so that it can be delivered to the desired location. The stent may be kept at low temperatures by circulating chilled saline solutions. The stent expands when the chilled saline is removed and it is exposed to higher temperatures within the patient's body, generally around thirty-seven degrees centigrade.

In preferred embodiments, each stent is fabricated from a single piece of alloy tubing. The tubing is laser cut, shape-set by placing the tubing on a mandrel, and heat-set to its desired expanded shape and size.

In preferred embodiments, the shape setting is performed in stages at five hundred degrees centigrade. That is, the stents are placed on sequentially larger mandrels and briefly heated to five hundred degrees centigrade. To minimize grain growth, the total time of exposure to a temperature of five hundred degrees centigrade is limited to five minutes. The stents are given their final shape set for four minutes at five hundred fifty degrees centigrade, and then aged to a temperature of four hundred seventy degrees centigrade to import the proper martensite to austenite transformation temperature, then blasted, as described in detail subsequently, before electropolishing. This heat treatment process provides for a stent that has a martensite to austenite transformation which occurs over a relatively narrow temperature range; for example, around fifteen degrees centigrade.

To improve the mechanical integrity of the stent, the rough edges left by the laser cutting are removed by combination of mechanical grit blasting and electropolishing. The grit blasting is performed to remove the brittle recast layer left by the laser cutting process. This layer is not readily removable by the electropolishing process, and if left intact, could lead to a brittle fracture of the stent struts. A solution of seventy percent methanol and thirty percent nitric acid at a temperature of minus forty degrees centigrade or less has been shown to work effectively as an electropolishing solution. Electrical parameters of the electropolishing are selected to remove approximately 0.00127 cm of material from the surfaces of the struts. The clean, electropolished surface is the final desired surface for attachment to the graft materials. This surface has been found to import good corrosion resistance, fatigue resistance, and wear resistance.

Figure 6:
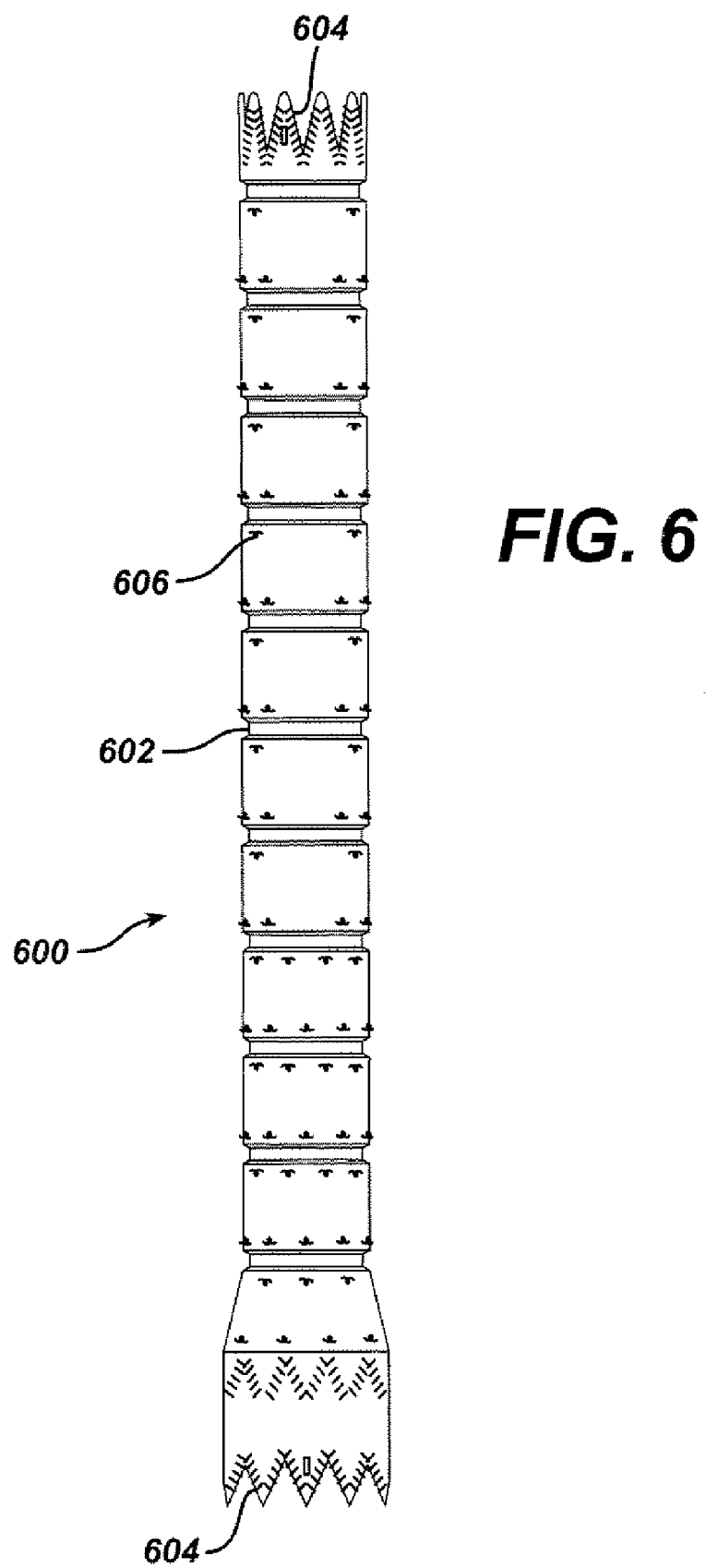
FIG. 6 is an elevational view of an endovascular graft in accordance with the present invention.

The graft material or component 600, as illustrated in FIG. 6, may be made from any number of suitable biocompatible materials, including woven, knitted, sutured, extruded, or cast materials comprising polyester, polytetrafluoroethylene, silicones, urethanes, and ultralight weight polyethylene, such as that commercially available under the trade designation SPECTRA™. The materials may be porous or nonporous. Exemplary materials include a woven polyester fabric made from DACRON™ or other suitable PET-type polymers.

In one exemplary embodiment, the fabric for the graft material is a forty denier (denier is defined in grams of nine thousand meters of a filament or yarn), twenty-seven filament polyester yarn, having about seventy to one-hundred end yarns per cm per face and thirty-two to forty-six pick yarns per cm face. At this weave density, the graft material is relatively impermeable to blood flow through the wall, but is relatively thin, ranging between 0.08 and 0.12 mm in wall thickness.

The graft component 600 is a single lumen tube and preferably has a taper and flared portion woven directly from the loom, as illustrated for the endovascular graft 300 shown in FIG. 3.

Prior to attachment of the graft component 600 to the stents 310, 320, 330, crimps are formed between the stent positions by placing the graft material on a shaped mandrel and thermally forming indentations in the surface. In the exemplary embodiment illustrated in FIGS. 3 and 6, the crimps 602 in the graft 400 are about two mm long and 0.5 mm deep. With these dimensions, the endovascular graft 300 can bend and flex while maintaining an open lumen. Also, prior to attachment of the graft component 600 to the stents 310, 320 330, the graft material is cut in a shape to mate with the end of each end stent.

As stated above, each of the stent segments 310, 320 and 330 is attached to the graft material 600. The graft material 600 may be attached to the stent segments 310, 320, 330 in any number of suitable ways. In one exemplary embodiment, the graft material 600 may be attached to the stent segments 310, 320, 330 by sutures.

The method of suturing stents in place is important for minimizing the relative motion or rubbing between the stent struts and the graft material. Because of the pulsatile motion of the vasculature and therefore the graft system, it is possible for relative motion to occur, particularly in areas where the graft system is in a bend, or if there are residual folds in the graft material, due to being constrained by the aorta or iliac arteries.

Ideally, each strut of each stent segment is secured to the graft material by sutures. In an exemplary embodiment, the suture material is blanket stitched to the stent segments at numerous points to securely fasten the graft material to the stent segments. As stated above, a secure hold is desirable in preventing relative motion in an environment in which the graft system experiences dynamic motion arising from pulsatile blood pressure, in addition to pulsation of the arteries that are in direct mechanical contact with the graft system. The stents nearest the aortic and iliac ends of the graft system (the uppermost first stent segment 310 and the third stent segment 330 respectively) are subject to the pulsatile motion arising from direct internal contact. These struts in particular should be well secured to the graft material. As illustrated in FIG. 6, the stitches 604 on the upper most first stent segment 310 are positioned along the entire zigzag arrangement of struts. The upper and lower apexes of the third stent segment may be stitched utilizing a similar configuration. It is difficult to manipulate the suture thread precisely around the struts that are located some distance away from an open end, accordingly, various other simpler stitches may be utilized on these struts, or no stitches may be utilized in these areas.

As illustrated in FIG. 6, each of the struts in the first stent segment 310 is secured to the graft material 600 which has been cut to match the shape of the stent segment 310. The blanket stitching 604 completely encircles the strut and bites into the graft material 600. Preferably, the stitch 604 encircles the strut at approximately five equally spaced locations. Each of the struts on each end of the third stent segment 330 is attached to the graft material, which has been cut to make the shape of the stent segment 330, in the same manner as the first stent segment 310.

A significant portion of the graft will not rest directly against vascular tissue. This portion of the graft will be within the dilated aneurysm itself. Therefore, this portion of the graft will not experience any significant pulsatile motion. For this reason, it is not necessary to secure the stent segments to the graft material as aggressively as the stent structure described above. Therefore, only point stitches 606 are necessary for securing these stents.

It is important to note that a wide variety of sutures are available. It is equally important to note that there are a number of alternative means for attaching the graft material to the stent, including welding, gluing and chemical bonding.

As described above with respect to suturing stents in place, it is important to minimize or substantially reduce the relative motion or rubbing between the stent struts and the graft material. This relative motion arises from pulsatile blood pressure in addition to the pulsation of the arteries that are in direct mechanical contact with the graft system.

The present invention is directed to a means for attaching graft material to stent structures in such a manner as to significantly reduce or substantially eliminate this relative motion. The means may be utilized in any of the stent structures described herein, including the stents forming the trunk section and bifurcated section of the anchoring and sealing component of the repair device and the first, second and third stent segments of the endovascular graft.

Figure 7:
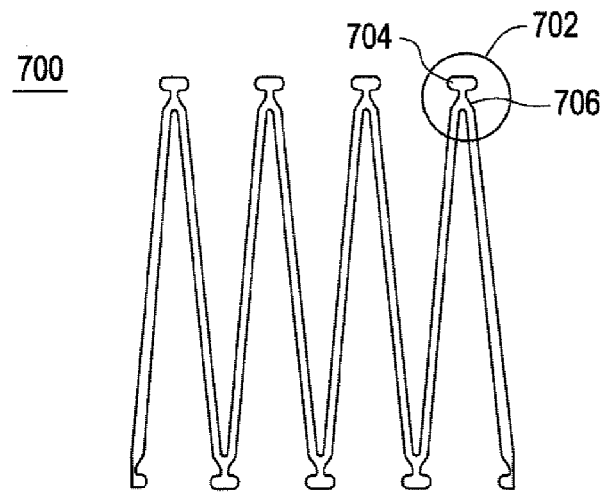
FIG. 7 is a diagrammatic representation of a stent segment having a first modified apex design in accordance with the present invention.
Figure 8A:
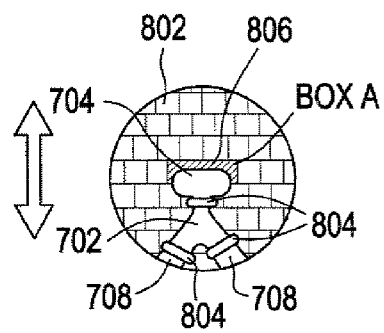
FIGS. 8A and 8B are diagrammatic representations of a portion of the modified apex as it is attached to the graft material in accordance with the present invention.
Figure 8B:
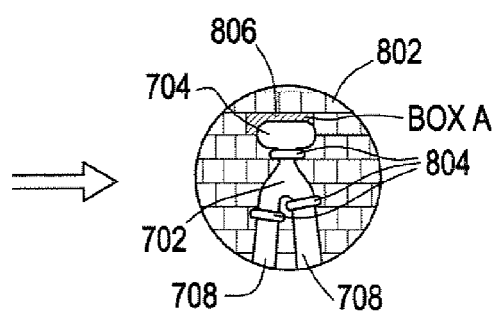

Referring to FIG. 7, there is illustrated an exemplary embodiment of a modified stent cell 700 design in accordance with the present invention. As shown, rather than a simple apex 334 as illustrated in FIG. 4, the modified stent cell 700 comprises a more complex or modified apex 702 that is designed to more securely attach the graft to the stent while allowing the graft material to move with the apex as is illustrated in FIGS. 8A and 8B and described subsequently. The modified apex 702 comprises a tab like structure 704 and a narrow neck structure 706. This configuration allows the sutures to be connected utilizing a delta stitch as described in more detail below. This modified apex 702 may comprise other suitable configurations and sizes so long as it allows for securely holding the delta stitch or any other stitch or attaching elements, and does not significantly impact the size of the overall device. The modified apex 702 may comprise radiopaque material such as tantalum and thus serve a dual role as holder and marker.

Referring now to FIGS. 8A and 8B, there is illustrated the more complex apex 702 relative to the graft material 802 forming the particular component. In both figures, the more complex modified apex 702 is secured to the graft material 802 by any suitable, non-biodegradable or non-bioerrodable suture material 804 utilizing a delta stitch. The delta stitch is so named because when looked at as a single entity, the stitching pattern forms a substantially delta configuration. As illustrated, the delta stitch suture 804 fits around two struts 708 and the narrow neck structure 706. With this configuration, the apex itself holds two legs of the delta stitch in position, and the combination of the narrow neck structure 706 along with the tab 704 holds the third leg of the delta stitch in position. It is important to note that any stitch may be utilized and that if so desired, the stitching material may be made out of a degradable material. Utilizing a degradable stitch material allows for an acute connection, but also allows for removal of a component if desired after the material degrades.

As set forth above, this unique arrangement not only holds the graft to the stent, but also allows for movement of the graft together with the stent, thereby ensuring minimal or substantially no relative movement. The black square 806 of the graft material 802 is always maintained in position behind the tab 704 even though the stent structure moves and changes shape. Without this relative movement, wear is reduced.

Figure 9A:
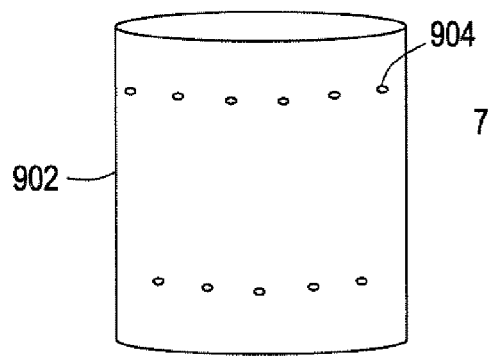
FIG. 9A is a diagrammatic presentation of a modified graft in accordance with the present invention.
Figure 9B:
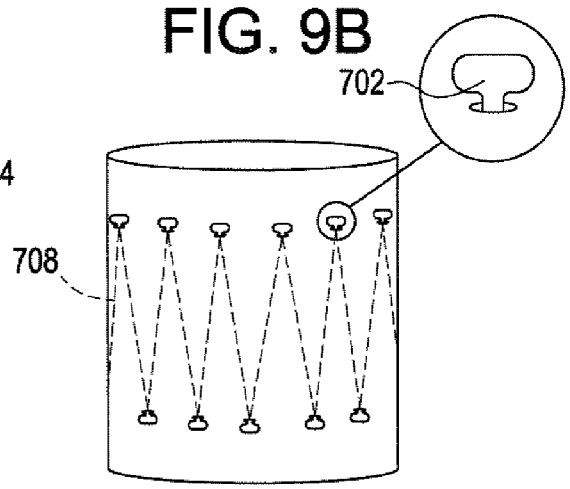
FIG. 9B is a diagrammatic representation of a modified stent-graft in accordance with the present invention.

In an alternative exemplary embodiment, the graft material itself may comprise openings for securing the more complex apex 702 illustrated in FIGS. 7, 8A and 8B. With this type of configuration, no sutures or other attachment means or elements may be required. FIG. 9A illustrates a substantially cylindrical section of graft material 902 comprising a plurality of openings or slits 904. These slits 904 are designed large enough for the tabs 704 of the stent to go through, but small enough to hold them in place as illustrated in FIG. 9B with the stent struts 708 shown in phantom.

Figure 10:
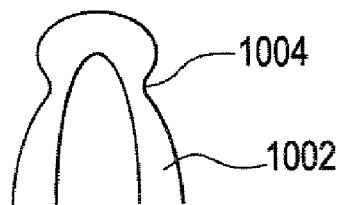
FIG. 10 is a diagrammatic representation of a stent segment having a second modified apex design in accordance with the present invention.
Figure 11:
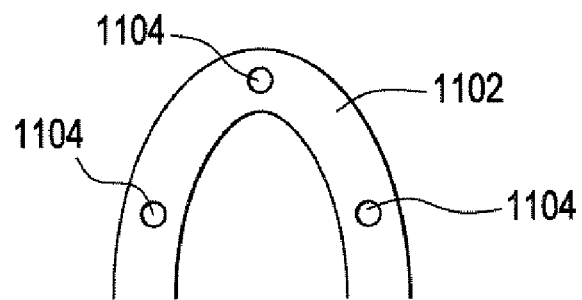
FIG. 11 is a diagrammatic representation of a stent segment having a third modified apex design in accordance with the present invention.
Figure 12:
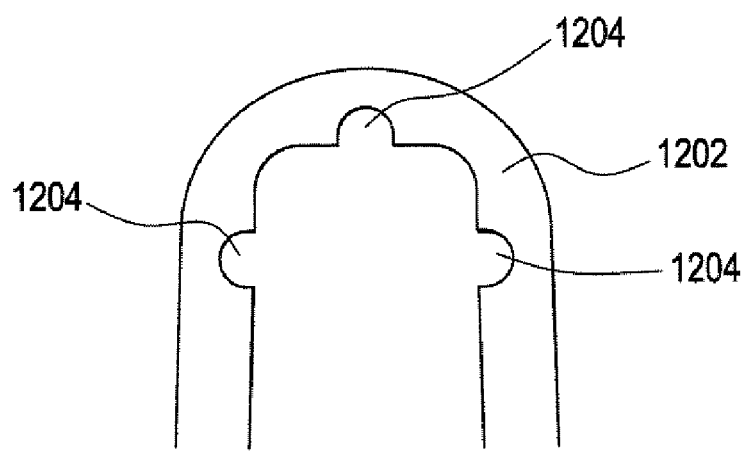
FIG. 12 is a diagrammatic representation of a stent segment having a fourth modified apex design in accordance with the present invention.

With respect to the exemplary embodiment illustrated in FIG. 7, a modified apex having a protrusion was utilized; however, in alternate exemplary embodiments, no protrusion may be required. For example, FIG. 10 illustrates a modified apex 1002 having a necked down region 1004 for holding a stitch or other suitable holding device such as a clip or staple. FIG. 11 illustrates a modified apex 1102 having multiple holes 1104 for securing a stitch or other suitable securing devices. In yet another alternate exemplary embodiment illustrated in FIG. 12, a modified apex 1202 may comprise a series of indents or notches 1204 to hold the attachment means. In each of these exemplary embodiments, there is no protrusion, just simply an attachment section. In addition, although shown and described as being on every apex, the present invention may be utilized on one, every other one or any combination of apexes.

Figure 13:
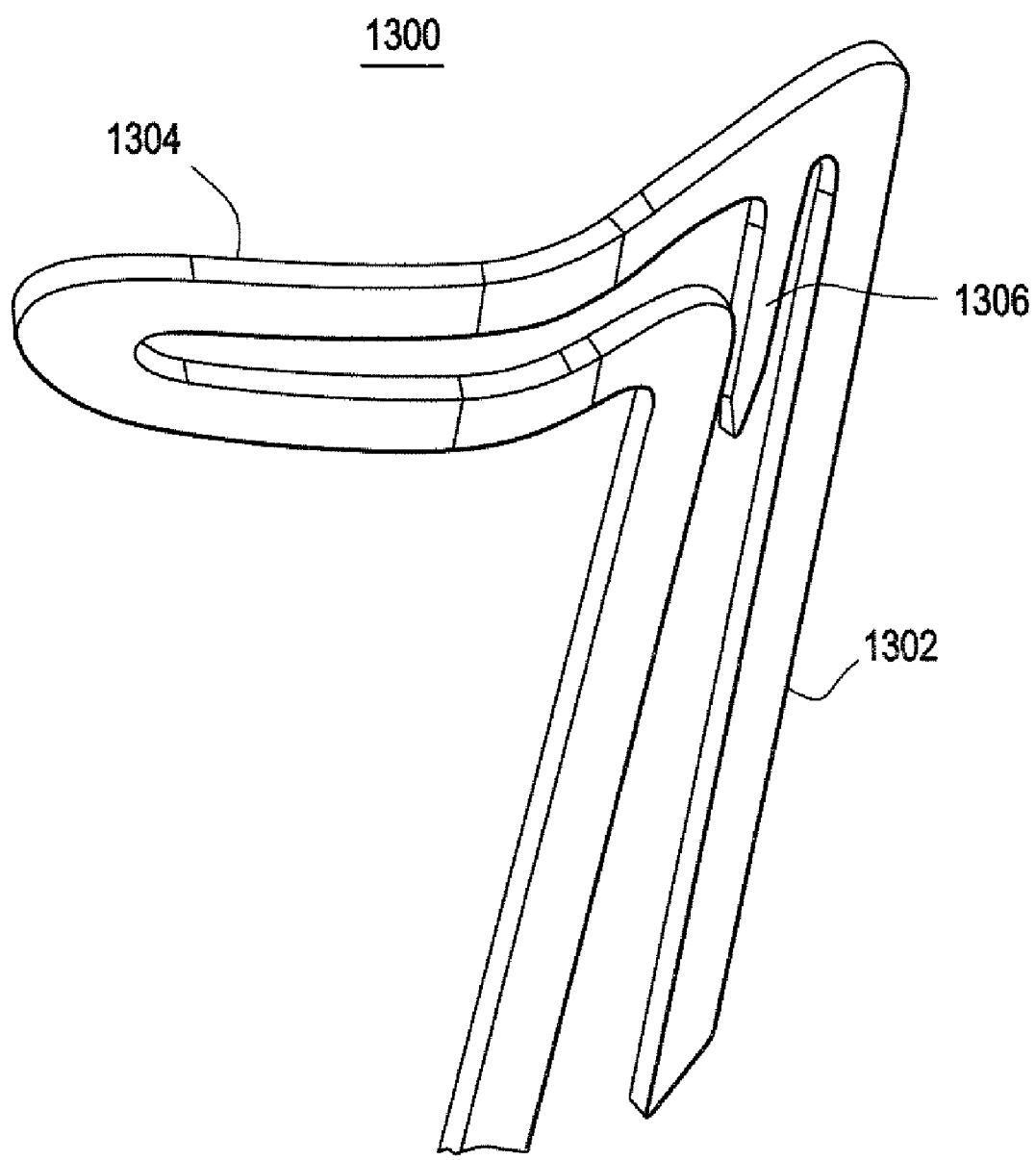
FIG. 13 is a first diagrammatic representation of a modified apex and fixation barb in accordance with the present invention.

In accordance with another exemplary embodiment, the present invention is directed to a modified apex having barbs for anchoring the stent-grafts into position. The barbs may be utilized with any of the stent structures described herein, but are preferably utilized with the anchoring and sealing component 100 illustrated in FIGS. 1 and 2. More specifically, the apexes of the substantially diamond shaped elements 112 would be modified as illustrated in FIG. 13. However, it is important to note that these barbs may be utilized with other cell structures in addition to diamonds, for example, a simple sinusoidal shape. The description below is only for illustrative purposes. FIG. 13 illustrates a modified apex 1300 having a first section 1302, a second section 1304 and a fixation barb 1306.

Figure 14:
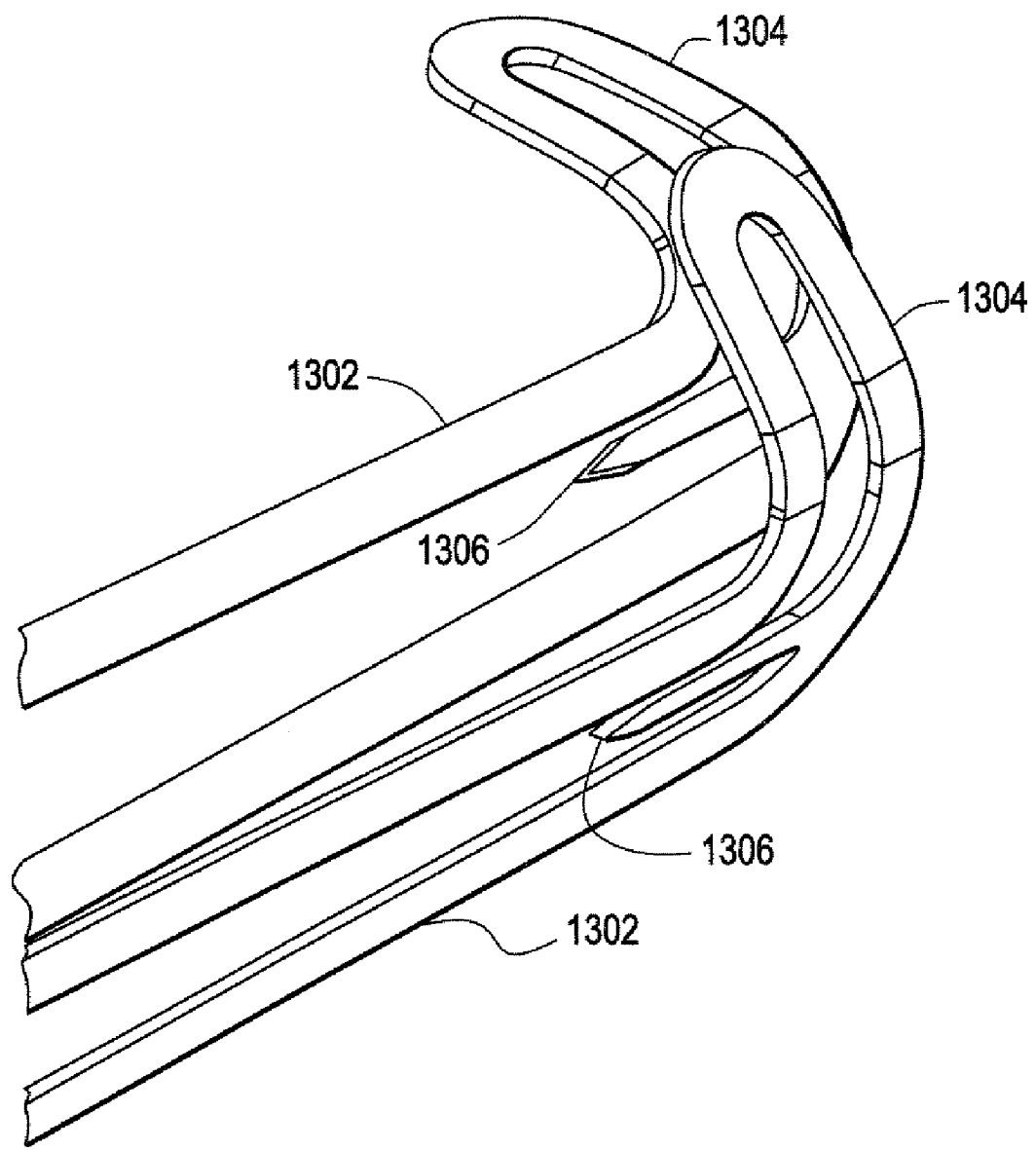
FIG. 14 is a second diagrammatic representation of a modified apex and fixation barb in accordance with the present invention.
Figure 15:
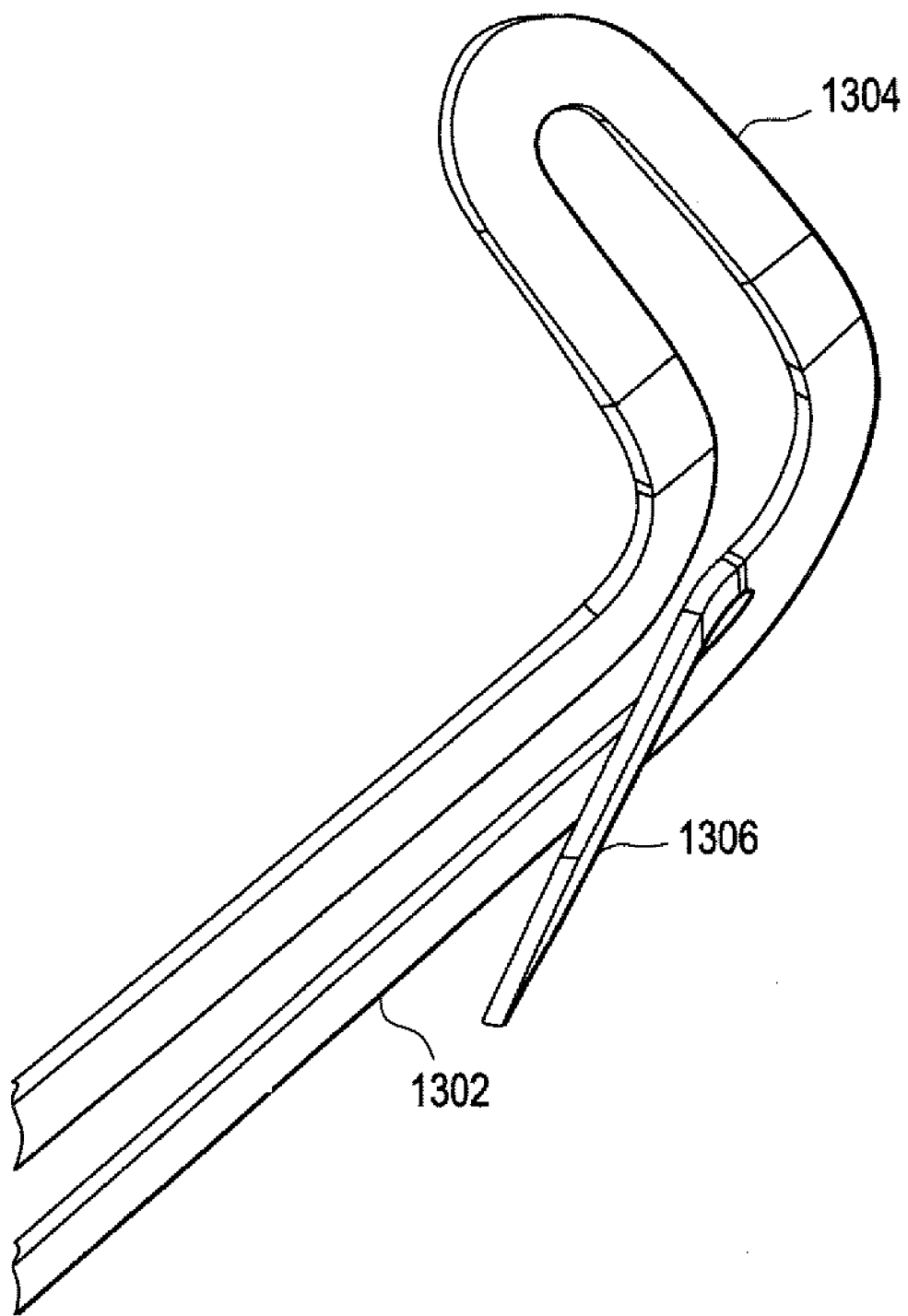
FIG. 15 is a third diagrammatic representation of a modified apex and fixation barb in accordance with the present invention.

This single modified apex 1300 is illustrated in the non-deployed state. FIG. 14 illustrates two modified apexes 1300 in the unexpanded or undeployed state and lends understanding as to how the invention works as well as its advantages. With this overlapping configuration of second sections 1304, the second section 1304 holds down the fixation barb 1306 in an adjacent apex. Once the device is deployed and the stent expands, the second sections 1304 no longer overlap thereby freeing the fixation barbs 1306 to extend outwardly and engage the vessel walls as illustrated in FIG. 15.

In one exemplary embodiment, the fixation barbs 1306 are shape set, as described herein, to angle away from the device for proper vessel wall engagement. In other words, the final configuration of the fixation barbs 1306 is programmed into the self-expanding alloy and then restrained for delivery as is explained in detail subsequently. In alternate exemplary embodiments, the apexes may be designed to twist or deform during expansion such that the deformation may be utilized to pull the fixation barbs 1306 into its final position thereby eliminating the need for shape setting.

This unique apex design offers a number of advantages including reducing the strain on the apex of the stent, reduced vessel stress due to the wider apex and the prevention of premature fixation barb release. The strain on each apex is reduced by opening the angle of the apex. As can be seen from a comparison of FIGS. 1 and 2 with FIG. 13, the radius of curvature of the modified apex is much greater, thereby reducing strain on the apex. Reduced vessel stress is achieved by the increased area of the second section 1304 of the modified apex 1300. This increase in area is spread out around the circumference of the vessel. Premature fixation barb release prevention is achieved by having the fixation barbs 1306 restrained during the entire prosthesis deployment and only released when the proximal or cranial end of the device is released.

Figure 16:
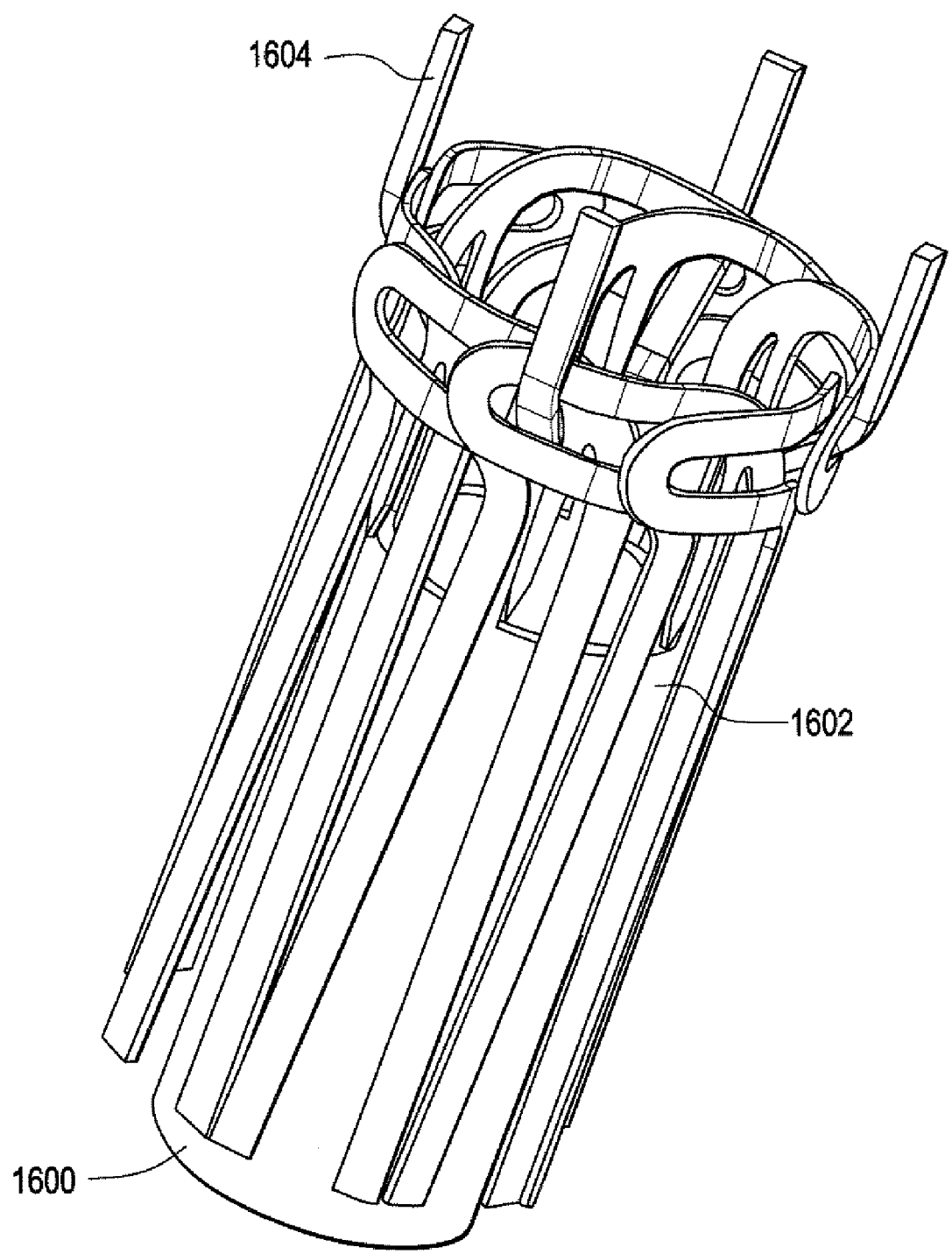
FIG. 16 is a diagrammatic representation of a stent deployment system for the modified apexes in accordance with the present invention.

FIG. 16 illustrates a stent section having modified apexes 1300 mounted on a delivery device. As illustrated, in the unexpanded or undeployed configuration, the second sections 1304 overlap and hold the fixation barbs 1306 in place. Essentially, the second sections 1304 are at substantially right angles to the first sections 1302. In one exemplary embodiment, the delivery device includes a hold down member that comprises a tubular member 1602 that slides coaxially over the inner member of a standard catheter based delivery system. The tubular member 1602 comprises a number of protrusions or fingers 1604 at its proximal end that engage the openings of the second sections 1304 and function to prevent them from opening. Essentially, the fingers 1604 are positioned through the openings of the second sections 1304.

In operation, once the device is positioned in the proper location, the outer sheath (not shown) is retracted. Once the outer sheath is retracted, last minute positioning of the device may be accomplished. Once positioning is complete, the tubular member 1602 is retracted by any suitable means, such as pull back wires, and the fingers 1604 are removed from the second members 1304 and thus the device is free to expand. This simple multi-finger release mechanism may be utilized to restrain all of the proximal apexes. Alternately, due to the overlapping design of the apexes, as few as a single finger may be utilized to restrain the entire circumference of the stent.

Accordingly, this unique design allows for the restraint and selective deployment of the cranial end of an endovascular prosthesis during delivery. It is also desirable to restrain the fixation barbs from deploying before the prosthesis has centered itself in the target vessel during deployment. Other devices have addressed these requirements individually. This device addresses both requirements. Essentially, this invention provides a means for restraining the cranial end of the supra-renal portion of an endoprosthesis that also effectively restrains the fixation barbs. With this design, the proximal end of the prosthesis may be restrained with one or more fingers attached to a cylindrical member that is pulled free from the assembly by the operator or physician in order to initiate the deployment of the proximal portion of the stent. It is important to note that if a single finger is utilized, a cylindrical member may not be needed. For example, as described above, a simple pull back mechanism may be utilized to retract the finger. This deployment of the stent will also release the fixation barbs, which will be shape set to angle away from the device for proper verbal wall engagement.

It is important to note that multiple barbs may be utilized in a well as various barb configurations.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An aneurysm repair system comprising:
    at least one substantially cylindrical stent segment, the at least one substantially cylindrical sent segment having modified apexes, the modified apexes including first sections, second sections and fixation barbs, the second sections being configured to overlap and restrain the fixation barb on an adjacent apex; and
    graft material affixed, via attachment elements, to at least a portion of the at least one substantially cylindrical stent segment.

2. The aneurysm repair system according to claim 1, wherein the attachment elements comprise sutures.

3. The aneurysm repair system according to claim 1, wherein the substantially cylindrical stent segment comprises a superelastic material.

4. The aneurysm repair system according to claim 3, wherein the superelastic material comprises a nickel-titanium alloy.

5. The aneurysm repair system according to claim 1, wherein the substantially cylindrical stent segment comprises a shape memory material.

6. The aneurysm repair system according to claim 5, wherein the shape memory material comprises a nickel-titanium alloy.

7. A stent comprising at least one substantially cylindrical stent segment having modified apexes, the modified apexes including first sections, second sections and fixation barbs, the second sections being configured to overlap and restrain the fixation barb on an adjacent apex.

8. The stent according to claim 7, wherein the modified apex is configured to reduce fatigue resistance at the apex.

9. A stent system comprising:
    at least one substantially cylindrical stent segment having modified apexes, the modified apexes including first sections, second sections and fixation barbs, the second sections being configured to overlap and restrain the fixation barb on an adjacent apex; and
    a securing mechanism having at least one protruding member configured for placement in at least one of the second sections and a hold down member connected on one end to the at least one protruding member and on the other end to a pull back member.

* * * * *